US009453813B2

(12) United States Patent
Brenneman et al.

(10) Patent No.: US 9,453,813 B2
(45) Date of Patent: *Sep. 27, 2016

(54) ELECTROCHEMICAL TEST SENSOR WITH LIGHT GUIDE

(71) Applicant: Ascensia Diabetes Care Holdings AG, Basel (CH)

(72) Inventors: Allen J. Brenneman, Goshen, IN (US); Dan O'Sullivan, Mount Vernon, NH (US)

(73) Assignee: Ascensia Diabeties Care Holdings AG, Basel (CH)

( * ) Notice: Subject to any disclaimer, the term of this patent is extended or adjusted under 35 U.S.C. 154(b) by 149 days.

This patent is subject to a terminal disclaimer.

(21) Appl. No.: 14/332,029

(22) Filed: Jul. 15, 2014

(65) Prior Publication Data

US 2014/0326599 A1 Nov. 6, 2014

Related U.S. Application Data

(63) Continuation of application No. 12/521,829, filed as application No. PCT/US2007/025407 on Dec. 12, 2007, now Pat. No. 8,815,079.

(60) Provisional application No. 60/905,421, filed on Mar. 7, 2007, provisional application No. 60/878,953, filed on Jan. 5, 2007.

(51) Int. Cl.
*G01N 27/327* (2006.01)
*A61B 5/145* (2006.01)
(Continued)

(52) U.S. Cl.
CPC ......... *G01N 27/3272* (2013.01); *A61B 5/1486* (2013.01); *A61B 5/14532* (2013.01); *C12Q 1/006* (2013.01); *C12Q 1/54* (2013.01)

(58) Field of Classification Search
CPC ............ C12Q 1/00; C12Q 1/02; C12Q 1/34; C12Q 1/54; G01N 27/327; G01N 27/3272
See application file for complete search history.

(56) References Cited

U.S. PATENT DOCUMENTS

| 4,904,037 A | 2/1990 | Imoto et al. |
| 5,120,420 A | 6/1992 | Nankai et al. |

(Continued)

FOREIGN PATENT DOCUMENTS

| EP | 1 557 664 A1 | 7/2005 |
| EP | 1 577 668 A2 | 9/2005 |

(Continued)

OTHER PUBLICATIONS

"Institute of Electrical and Electronics Engineers," *The IEEE Standard Dictionary of Electrical and Electronics Terms*, New York, N.Y. ($6^{th}$ Ed. 1997), pp. 725-726 (2 pages).

(Continued)

*Primary Examiner* — Jennifer Dieterle
(74) *Attorney, Agent, or Firm* — Nixon Peabody LLP (57) ABSTRACT

An electrochemical test sensor for detecting the analyte concentration of a fluid test sample includes a base, a dielectric layer, a reagent layer, a light guide area, and a lid. The base provides a flow path for the test sample having on its surface a counter electrode and a working electrode adapted to electrically communicate with a detector of electrical current. The dielectric layer forms a dielectric window therethrough. The reagent layer includes an enzyme that is adapted to react with the analyte. The lid is adapted to mate with the base and to assist in forming a capillary space with an opening for the introduction of the test sample thereto. The light guide area transmits light towards the capillary space.

20 Claims, 5 Drawing Sheets

(51) Int. Cl.
*A61B 5/1486* (2006.01)
*C12Q 1/00* (2006.01)
*C12Q 1/54* (2006.01)

(56) References Cited

U.S. PATENT DOCUMENTS

| | | |
|---|---|---|
| 5,320,732 A | 6/1994 | Nankai et al. |
| 5,519,803 A | 5/1996 | Shiono et al. |
| 5,582,697 A | 12/1996 | Ikeda et al. |
| 5,660,791 A | 8/1997 | Brenneman et al. |
| 6,423,011 B1 | 7/2002 | Arulkumaran et al. |
| 6,514,460 B1 | 2/2003 | Fendrock |
| 6,535,680 B1 | 3/2003 | Hori et al. |
| 7,118,668 B1 | 10/2006 | Edelbrock et al. |
| 7,122,102 B2 | 10/2006 | Wogoman |
| 7,125,481 B2 | 10/2006 | Musho et al. |
| 2002/0053523 A1* | 5/2002 | Liamos ............ G01N 27/3272 205/787 |
| 2005/0009126 A1 | 1/2005 | Andrews et al. |
| 2005/0176133 A1 | 8/2005 | Miyashita et al. |
| 2005/0201897 A1 | 9/2005 | Zimmer et al. |
| 2005/0265094 A1* | 12/2005 | Harding ............ G01N 27/3273 365/203 |
| 2008/0309623 A1 | 12/2008 | Hotelling et al. |

FOREIGN PATENT DOCUMENTS

| | | |
|---|---|---|
| EP | 1 596 189 A2 | 11/2005 |
| EP | 2 117 421 B1 | 12/2007 |
| WO | WO 2006/014410 A1 | 2/2006 |
| WO | WO 2008/085251 A1 | 7/2008 |

OTHER PUBLICATIONS

PCT International Search Report for International Application No. PCT/US2007/025407 dated May 27, 2008 (4 pages).
PCT International Written Opinion for International Application No. PCT/US2007/025407 dated May 27, 2008 (7 pages).

* cited by examiner

Fig. 5

ELECTROCHEMICAL TEST SENSOR WITH LIGHT GUIDE

CROSS-REFERENCE AND CLAIM OF PRIORITY TO RELATED APPLICATIONS

This application is a continuation of U.S. patent application Ser. No. 12/521,829, which was filed on Jun. 30, 2009, now allowed, which is a U.S. national phase of International Application No. PCT/US2007/025407, which was filed on Dec. 12, 2007, and claims priority to U.S. Provisional Patent Application Nos. 60/905,421, filed Mar. 7, 2007, and 60/878,953, filed Jan. 5, 2007, all of which are incorporated herein by reference in their respective entireties.

FIELD OF THE INVENTION

The present invention relates generally to electrochemical test sensors, and more specifically to a test sensor that is adapted to determine the concentration of an analyte.

BACKGROUND OF THE INVENTION

Medical conditions such as diabetes require a person afflicted with the condition to regularly self-monitor that person's blood-glucose concentration level. The purpose of monitoring the blood, glucose concentration level is to determine the person's blood glucose concentration level and then to take corrective action, based upon whether the level is too high or too low, to bring the level back within a normal range. The failure to take corrective action may have serious medical implications for that person.

One method of monitoring a person's blood glucose level is with a portable testing device. The portable nature of these devices enables users to conveniently test their blood glucose levels at different locations. One type of device utilizes an electrochemical test sensor to harvest and analyze the blood sample. The test sensor typically includes a capillary channel to receive the blood sample and a plurality of electrodes. There are dines when a person needs to monitor their blood glucose concentration level in a setting without a great deal of ambient lighting. There are other times when a person who monitors their blood glucose concentration level may have difficulty locating where the blood sample will be collected by the test sensor. Thus, there exists a need for an electrochemical test sensor capable of allowing light to be transmitted through the test sensor to both help the person when testing in an area with low ambient lighting, and allowing the person to know what area of the test sensor the blood sample collection occurs.

SUMMARY OF THE INVENTION

According to one embodiment, an electrochemical test sensor for detecting the concentration of an analyte in a fluid test sample comprises a base, dielectric layer, a reagent layer and a lid. The base provides a flow path for the fluid test sample having on its surface a counter electrode and a working, electrode adapted to electrically communicate with a detector of electrical current. The dielectric layer forms a dielectric window therethrough. The reagent layer includes an enzyme that is adapted to react with the analyte. The lid is adapted to mate with the base and to assist in forming a capillary space with an opening for the introduction of the fluid test sample thereto. The lid includes a light guide area that transmits light from a first end of the test sensor towards the capillary space.

According to one embodiment, an electrochemical test sensor for detecting the concentration of an analyte in a fluid test sample comprises a base, dielectric layer, a reagent layer, a light guide layer, and a lid. The base provides a flow path for the fluid test sample having on its surface a counter electrode and a working electrode adapted to electrically communicate with a detector of electrical current. The dielectric layer forms a dielectric window therethrough. The reagent layer includes an enzyme that is adapted to react with the analyte. The lid is adapted to mate with the base and to assist in forming a capillary space with an opening for the introduction of the fluid test sample thereto. The light guide layer is adapted to transmit light form a first end of the test sensor towards the capillary space. The light guide layer, the dielectric layer, and the reagent layer are located between the base and the lid.

According to one method, an analyte concentration in a fluid sample is determined with a test sensor. An electrochemical test sensor is provided that includes a base, a dielectric layer, a reagent layer, a light guide area, and a lid. The base provides a flow path for the fluid test sample having on its surface a counter electrode and a working electrode adapted to electrically communicate with a detector of electrical current. The dielectric layer forms a dielectric window therethrough. The reagent layer includes an enzyme that is adapted to react with the analyte. The lid is adapted to mate with the base and to assist in forming a capillary space with an opening for the introduction of the fluid test sample thereto. The light guide area is adapted to transmit light through the light guide area towards the capillary space. The dielectric layer and the reagent layer are located between the base and the lid. The light guide transmits light through the light guide area towards the fluid sample. The light transmitted through the light guide area illuminates the fluid sample. The reagent layer contacts the fluid sample via the capillary space. An electrical signal is generated in the test sensor in response to the presence of the analyte. A level of the analyte is determined from the electrical signal.

DESCRIPTION OF ILLUSTRATED EMBODIMENTS

The present invention is directed to an electrochemical test sensor meter that is adapted to be placed into a meter or an instrument and assist in determining, an analyte concentration in a body fluid sample. The electrochemical sensor of the present invention assists in reducing the volume of the fluid sample needed to properly determine the analyte concentration. The body fluid sample may be collected with a lancing device.

Examples of the types of analytes that may be collected include glucose, lipid profiles (e.g., cholesterol, triglycerides, LDL and HDL), microbumin, hemoglobin $A_{1C}$, fructose, lactate, or bilirubin. It is contemplated that other analyte concentrations may also be determined. The analytes may be in, for example, a whole blood sample, a blood serum sample, a blood, plasma sample, other body fluids like ISF (interstitial fluid) and urine, and non-body fluids. As used within this application, the term "concentration" refers to an analyte concentration, activity (e.g., enzymes and electrolytes), titers (e.g., antibodies), or any other measure concentration used to measure the desired analyte.

Figure 1:
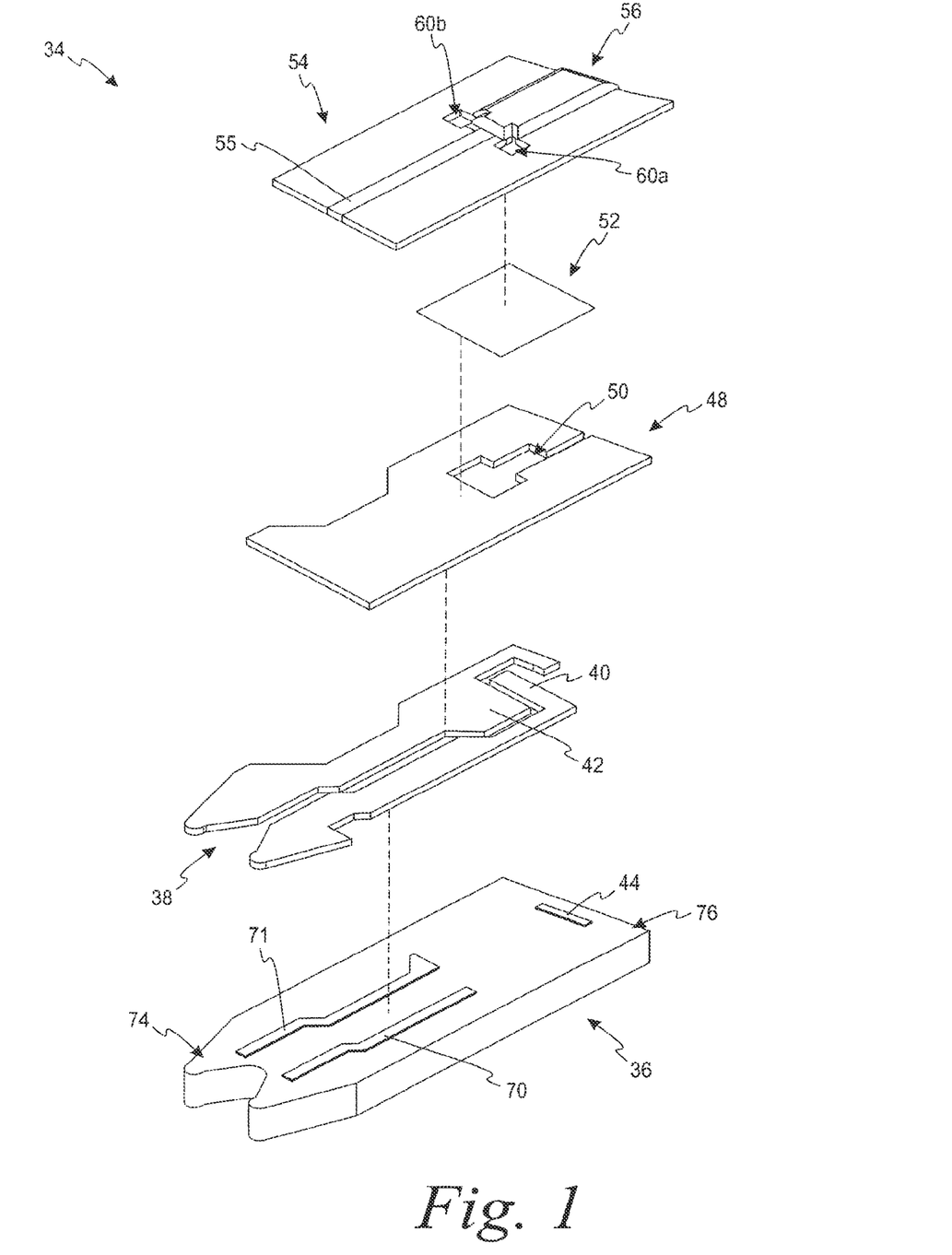
FIG. 1 is an exploded view of an electrochemical test sensor according one embodiment.
Figure 2:
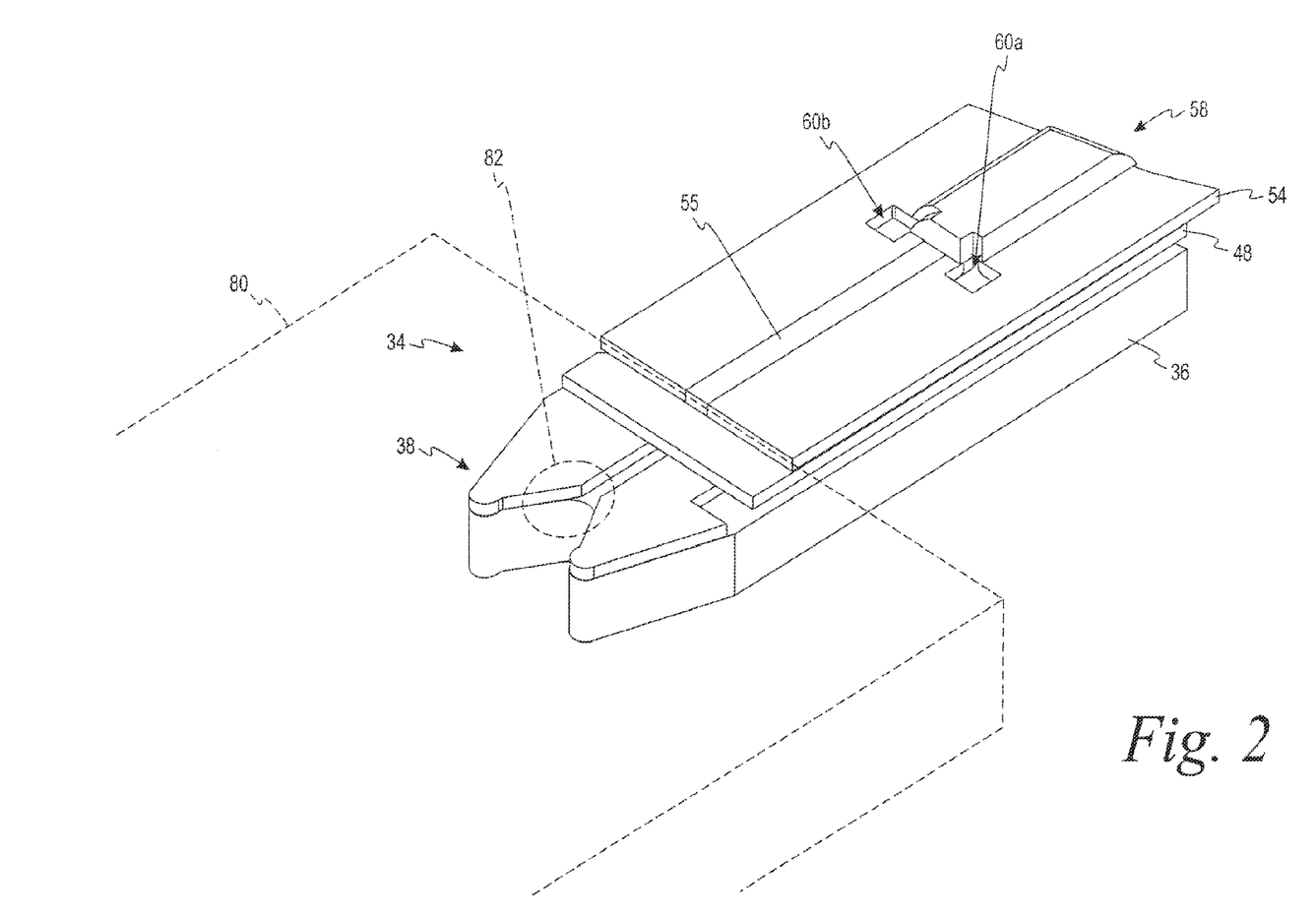
FIG. 2 is a perspective view of the assembled electrochemical test sensor of FIG. 1 in a portion of an illustrative test meter.
Figure 3:
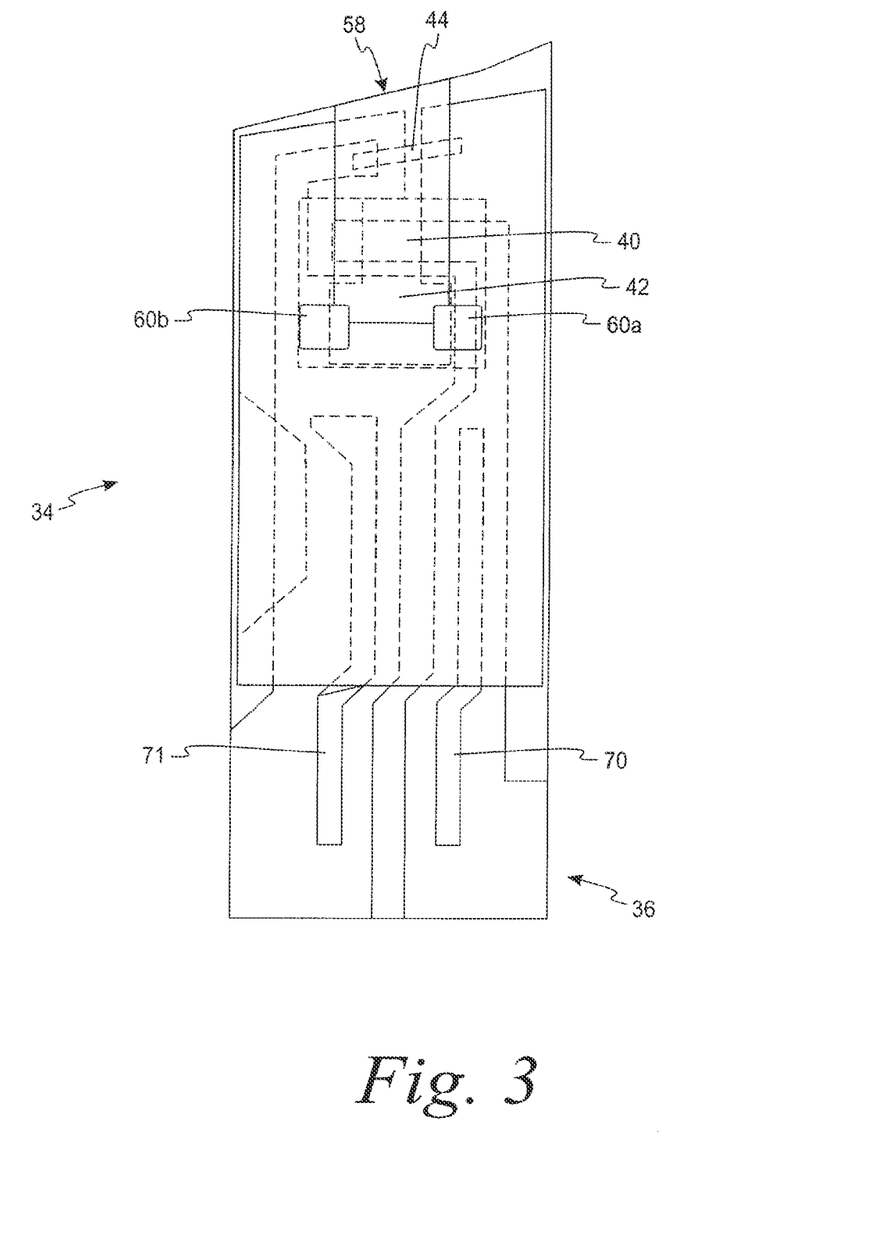
FIG. 3 is a top view of the assembled electrochemical test sensor of FIG. 1.

Referring initially to FIGS. 1-3, an electrochemical test sensor 34 includes an insulating base 36, a meter-contact area 38, a plurality of electrodes 40, 42 and 44, a dielectric layer 48, a reagent layer 52 and a lid 54. The plurality of electrodes in FIG. 3 includes a working electrode 40, a counter electrode 42 and a trigger electrode 44. The electrochemical test sensor 34 may be printed in sequence such as by a screen-printing technique. It is contemplated that the electrochemical test sensor may be formed by other methods.

The lid 54 includes a light guide area 55. The light guide area 55 is translucent or transparent to allow light to transmitted through the light guide area from a first end 74 of the test sensor 34 to a second end 76 of the test sensor. A test meter 80 (a portion of which is shown illustratively in FIG. 2) that the test sensor 34 is placed into features a light source 82 (FIG. 2), such as, for example, a light emitting diode (LED), near where the first end 74 interacts with the test sensor 34. The light from the light source 82 passes through light guide area 55 to the second end 76 of the test sensor 34, illuminating a capillary channel 58 (FIG. 2) of the test sensor 34. By illuminating the capillary channel 58 (FIG. 2), a user may more accurately position the test sensor 34 to a sample to be tested, such as a drop of blood on the users finger.

It is contemplated that the light guide area 55 may vary in width from the first end 74 to the second end 76 of the test sensor 34. The width of the light guide area 55 at the second end 76 of the test sensor 34 may be wider than the width of the light guide 55 are at the first end 74 of the test sensor 34 to allow more light to be visible to a user.

The light guide 55 may be made from a variety of materials. Non-limiting examples of materials to be utilized in forming the light guide 55 include acrylic, Polyethylene Terephthalate (PET), polycarbonate, or any other transparent or translucent polymeric material. Opaque areas surround the light guide 55 to allow a greater amount of light to transmit through the light guide 55.

The function of the reagent layer 52 of FIG. 1 is to convert an analyte (e.g., glucose) in the fluid test sample, stoichiometrically into a chemical species that is electrochemically measurable, in terms of electrical current it produces, by the components of the working electrode 40 and the counter electrode 42. The reagent layer 52 typically includes an enzyme and an electron acceptor. The enzyme reacts with the analyte to produce mobile electrons on the working and counter electrodes 40, 42. For example, the reagent layer may include glucose oxidase or glucose dehydrogenase if the analyte to be determined is glucose. The enzyme in the reagent layer 52 may be combined with a hydrophilic polymer such as polyethylene oxide) or other polymers such as polyethylene oxide (PEO), hydroxyethyl cellulose (HEC), carboxymethylcellulose (CMC) and polyvinyl acetate (PVA). The electron acceptor (e.g., ferricyanide salt) carries the mobile electrons to the surface of the working electrode 40.

The dielectric layer 48 of FIG. 1 limits the electrical area that is ultimately formed. Specifically, the dielectric layer 48 of FIG. 1 forms a dielectric window 50 that defines the working electrode 40 and assists in partially defining the counter electrode 42 as will be discussed below. The dielectric window 50 includes a first dielectric window section 50a, a second dielectric window section 50b and a third dielectric window section 50c. The dielectric layer may be formed by a variety of methods such as printing or die-cutting of a pressure-sensitive adhesive. It is contemplated that the dielectric layer may be formed by other methods.

The working electrode 40 and the counter electrode 42 assist in electrochemically determining the analyte concentration. In one embodiment, the working electrode 40 and the counter electrode 42 comprise a mixture of amorphous and graphite forms of carbon that is chosen to be electrochemically active and provide a low electrical resistance path between the electrodes and the meter or instrument with which they are in operative connection via the meter-contact area 38. In another embodiment, the working electrode 40 and the counter electrode 42 comprises a mixture of carbon and silver. It is contemplated that the working electrode and counter electrode may be made of other materials that assist in providing an electrical path to the meter or instrument with which they are in operative connection. It is contemplated that additional conductors may be added. For example, in FIG. 1, first and second conductors 70, 71 comprise a highly conductive carbon-silver ink that may be printed to further reduce the electrical resistance from the working and counter electrodes 40, 42 to the meter-contact area 38.

In the electrochemical sensor 34 of FIG. 1, the optional trigger electrode 44 assists in determining whether a sufficient fluid sample (e.g., blood) has been placed on the electrochemical test sensor 34. It is contemplated that an electrochemical sensor may include other electrodes such as an underfill electrode, hematocrit-detection electrode or other electrodes.

Referring still to FIG. 1, the lid 54 forms a concave space 56 over the base 36 and the components located thereon eventually form a capillary space or channel (see capillary space or channel 58 of FIG. 2). It is contemplated that the entire concave space 56 is part of the light guide 55. The lid 54 may be formed by embossing a flat sheet of deformable material and then joining the lid 54 and the base 36 in a sealing operation. The material forming the lid 54 may be a deformable polymeric sheet material (e.g., polycarbonate or au embossable grade of polyethylene terphthalate), or a glycol modified polyethylene terephthalate. It is contemplated that other materials may be used in forming the lid.

The material forming the lid 54 may be punctured to provide at least one air vent 60a,b. The air vents 60a,b are desirably because they assist in preventing or inhibiting air-lock. By preventing or inhibiting air-lock, a fluid sample is better able to enter the capillary channel 58 in a timely manner.

Suitable materials for the insulating base 36 of FIG. 1 include polymeric materials, such as polycarbonate, polyethylene terephthalate, dimensionally stable vinyl and acrylic polymers, and blends thereof. The insulating base may be formed from metal foil structures such as a nylon/aluminum/polyvinyl chloride laminate. It is contemplated that other materials may be used in forming the insulating base.

The lid 54 and the base 36 may be sealed together by a variety of methods. For example, the lid 54 and the base 36 may be sealed together by sonic welding in which the base 36 and the lid 54 are first aligned and then pressed together between a vibratory heat sealing member or horn and a stationary jaw. In this method, the horn is shaped such that contact is made only with the flat, non-embossed regions of the lid 54. Ultrasonic energy from a crystal or other transducer is used to excite vibrations in the metal horn. This mechanical energy is dissipated as heat in the polymeric joint allowing the bonding of the thermoplastic materials. In another method, the lid 54 and the base 36 are joined by using an adhesive material on the underside of the lid 54. It is contemplated that other methods may be used to attached the lid and the base.

Figure 4:
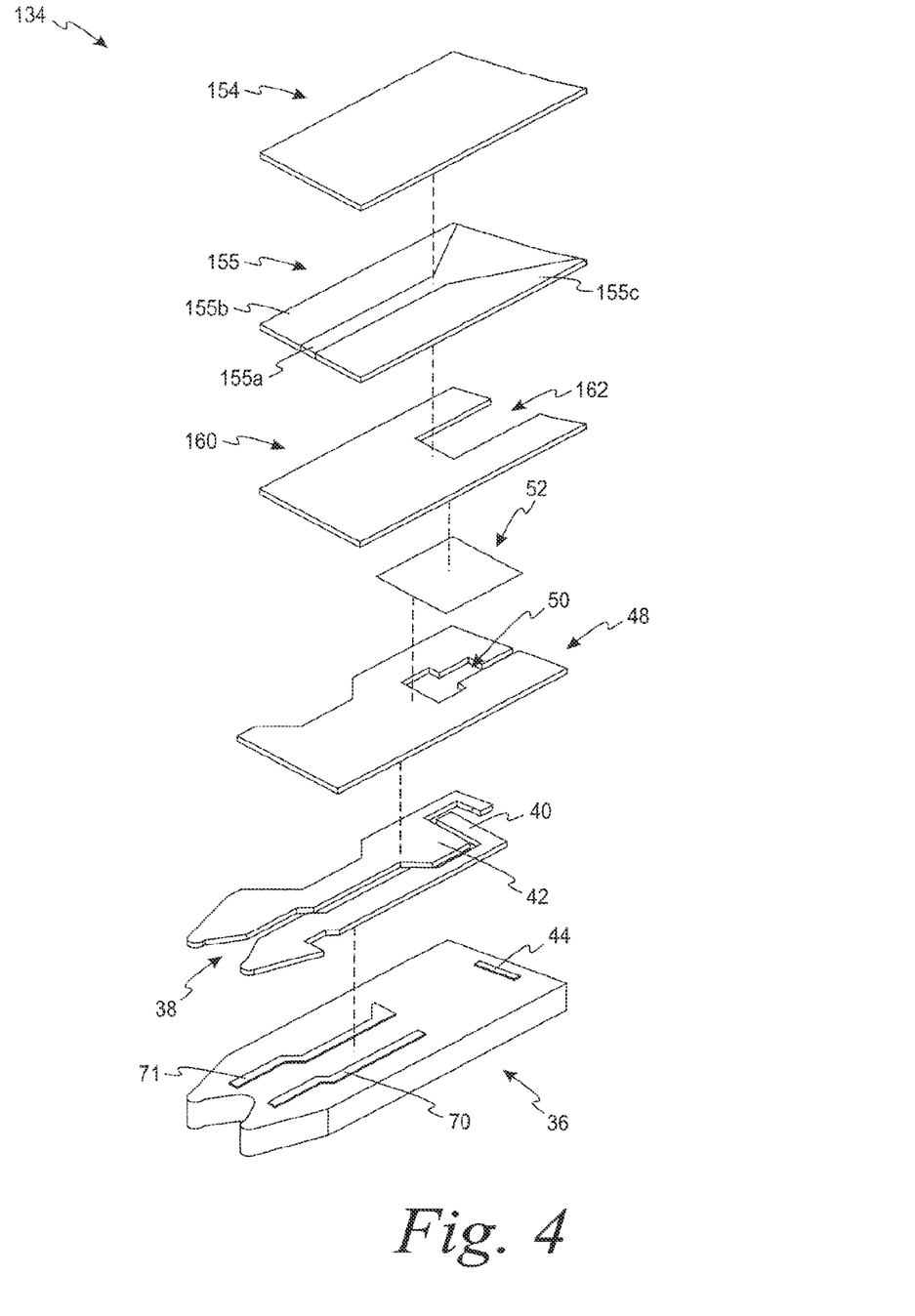
FIG. 4 is an exploded view of an electrochemical test sensor including a spacer according to one embodiment.

Turning now to FIG. 4, an electrochemical test sensor 134 according to another embodiment is shown. The electrochemical test sensor 134 includes the base 36, a meter-contact area 38, the working electrode 40, the counter electrode 42, and the reagent layer 52. The electrochemical test sensor 134 further includes a lid 154, a light guide layer 155, and a spacer 160.

The light guide 155 has a similar purpose to the light guide 55 previously described in connection with FIG. 1. The light guide 155 has a first area 155*a* that is generally transparent or translucent, as well as a second area 155*b* and a third area 155*c* that are generally opaque. Light is guided from a source within a test meter through the light guide 155 towards a capillary channel of the test sensor 134. The light allows a user to better position a sample to be tested relative to the test sensor 134. The light passing through the light guide 155 will also provide a user with more ambient light near the test meter, so that a user may be able to better observe aspects of the testing, such as a size of a blood drop that may be located on a user's finger. The light guide 155 may be made from acrylic, or other polymeric materials.

The spacer 160 includes a spacer opening 162 formed therein. The spacer opening 162 assists in forming the capillary channel or space when the lid 154 is mated with the spacer 160 and the base 36. The electrochemical test sensor 134 functions in much the same way as electrochemical test sensor 34 with the main differences being the method of forming the spacer opening 162 as compared to the concave space 48, and a separate component for the light guide 155.

Figure 5:
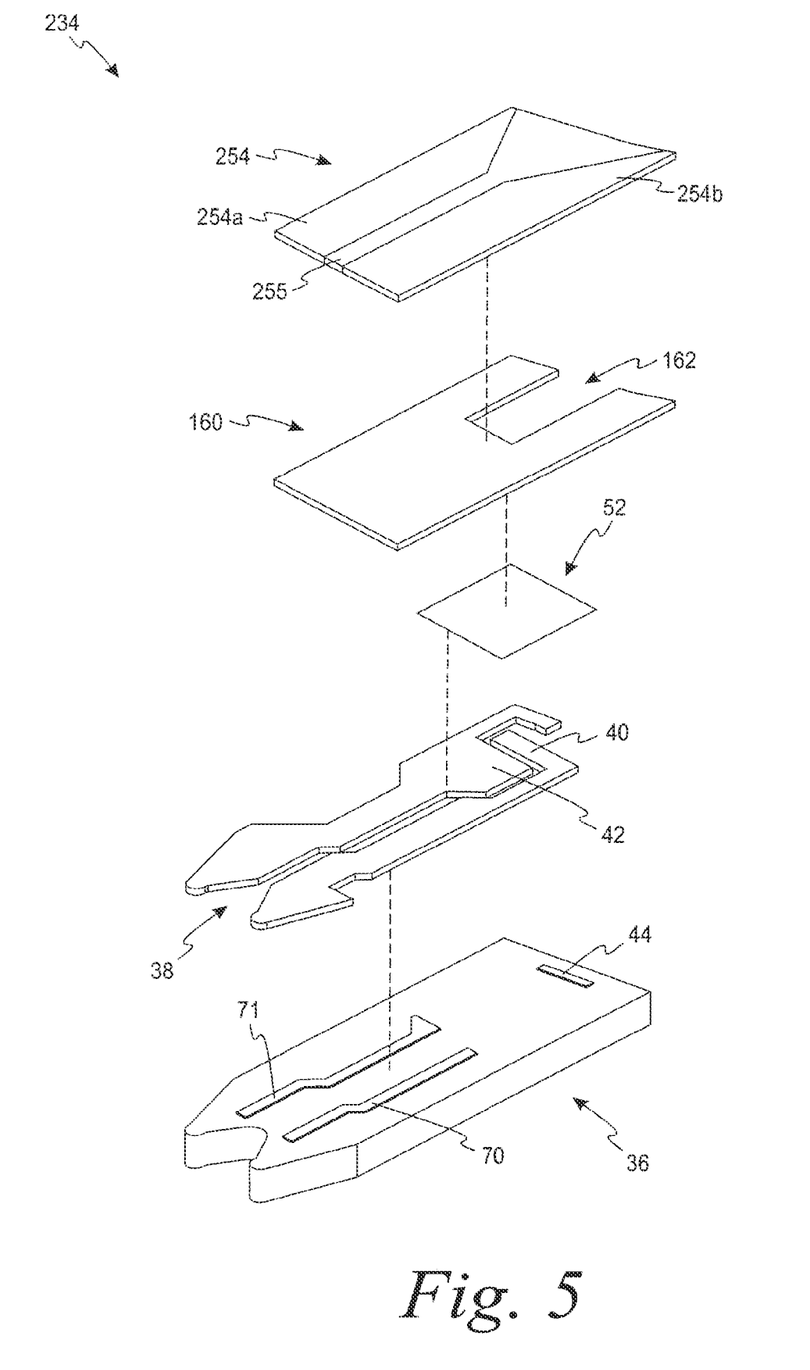
FIG. 5 is an exploded view of an electrochemical test sensor including a spacer according to another embodiment.

Referring to FIG. 5, another electrochemical test sensor (electrochemical test sensor 234) is depicted. The electrochemical test sensor 234 functions in a similar manner as discussed above in connection with electrochemical test sensors 34, 134. The electrochemical test sensor 234 is similar to the electrochemical test sensor 134 except that the electrochemical test sensor 234 does not include a dielectric layer, and a light guide area 255 is present in a lid 254 of the test sensor 234, not a separate layer. The light guide area 255 of the lid 254 is transparent or translucent and adapted to guide light through the test sensor 234 towards a capillary channel. The lid 254 has a first opaque area 254*a* and a second opaque area 254*b* located laterally of the light guide area 255.

It is further contemplated according to an alternative embodiment that a test sensor may contain chemicals that react to generate light that is transmitted through a light guide area of the test sensor. According to such an embodiment, no additional light source within a test meter would be required.

It is also contemplated according to another alternative embodiment that a test sensor adapted for optical testing, as opposed to electrochemical testing, may include a light guide similar to the embodiments depicted in FIGS. 1-5.

Embodiment A

An electrochemical test sensor for detecting the concentration of an analyte in a fluid test sample, the electrochemical test sensor comprising:

a base that provides a flow path for the fluid test sample having on its surface a counter electrode and a working electrode adapted to electrically communicate with a detector of electrical current;

a dielectric layer forming a dielectric window therethrough;

a reagent layer including an enzyme that is adapted to react with the analyte; and a lid adapted to mate with the base and to assist in forming a capillary space with an opening for the introduction of the fluid test sample thereto, wherein the lid includes a light guide area adapted to transmit light from a first end of the test sensor towards the capillary space.

Embodiment B

The electrochemical test sensor of embodiment A wherein the lid further forms at least one air vent.

Embodiment C

The electrochemical test sensor of embodiment A wherein the light guide area of the lid is transparent.

Embodiment D

The electrochemical test sensor of embodiment A wherein the light guide area of the lid is translucent.

Embodiment E

The electrochemical test sensor of embodiment A wherein the light guide area of the lid comprises a polymeric material.

Embodiment F

The electrochemical test sensor of embodiment E wherein the light guide area of the lid comprises acrylic.

Embodiment G

The electrochemical test sensor of embodiment A wherein the reagent layer includes glucose oxidase.

Embodiment H

Time electrochemical test sensor of embodiment A wherein the reagent layer includes glucose dehydrogenase.

Embodiment I

The electrochemical test sensor of embodiment A wherein the volume of the capillary space is less than about 1 µL.

Embodiment J

The electrochemical test sensor of embodiment A further including a spacer, the spacer being located between the lid and the reagent layer.

Embodiment K

An electrochemical test sensor for detecting the concentration of an analyte in a fluid test sample, the electrochemical test sensor comprising:

a base that provides a flow path for the fluid test sample having on its surface a counter electrode and a working electrode adapted to electrically communicate with a detector of electrical current;

a dielectric layer forming a dielectric window therethrough;

a reagent layer including an enzyme that is adapted to react with the analyte;

a lid adapted to mate with the base and to assist in forming a capillary space with an opening for the introduction of the fluid test sample thereto; and a light guide layer adapted to transmit light from a first end of the test sensor towards the capillary space, wherein the light guide layer, the dielectric layer, and the reagent layer are located between the base and the lid.

Embodiment L

The electrochemical test sensor of embodiment K wherein the light guide layer has a first area that is transparent.

Embodiment M

The electrochemical test sensor of embodiment L wherein the light guide layer as a second area and a third area that are opaque.

Embodiment N

The electrochemical test sensor of embodiment K wherein the light guide layer has a first area that is translucent.

Embodiment O

The electrochemical test sensor of embodiment L wherein the light guide layer has a second, area and a third area that are opaque.

Embodiment P

The electrochemical test sensor of embodiment K wherein the lid further forms at least one air vent.

Embodiment Q

The electrochemical test sensor of embodiment K wherein the reagent layer includes glucose oxidase.

Embodiment R

The electrochemical test sensor of embodiment K wherein the reagent layer includes glucose dehydrogenase.

Embodiment S

The electrochemical test sensor of embodiment K wherein the volume of the capillary space is less than about 1 µL.

Embodiment T

The electrochemical test sensor of embodiment K further including a spacer, the spacer being located between the light guide layer and the reagent layer.

Process U

A method for determining the concentration of an analyte in a fluid sample with a test sensor, the method comprising the acts of:

providing an electrochemical test sensor including a base, a dielectric layer, a reagent layer, a light guide area, and a lid, the base providing a flow path for the fluid test sample having on its surface a counter electrode and a working electrode adapted to electrically communicate with a detector of electrical current, the dielectric layer forming a dielectric window therethrough, the reagent layer including an enzyme that is adapted to react with the analyte, the lid being adapted to mate with the base and to assist in forming a capillary space with an opening for the introduction of the fluid test sample thereto, the light guide area being adapted to transmit light through the light guide area towards the capillary space, the dielectric layer and the reagent layer being located between the base and the lid;

transmitting light through the light guide area towards the fluid sample;

illuminating the fluid sample with the light transmitting through the light guide area contacting the reagent layer with the fluid sample via the capillary space;

generating an electrical signal in the test sensor in response to the presence of the analyte; and determining a level of the analyte from the electrical signal.

Process V

The method of process U wherein the analyte is glucose.

Process W

The method of process U wherein the light guide area is part of the lid.

Process X

The method of process U wherein the light guide area is part of a light guide layer.

Process Y

The method of process U wherein the light guide area is transparent.

Process Z

The method of process U wherein the light guide area is translucent.

Process AA

The method of process U wherein the light guide area comprises acrylic.

Process BB

The method of process LI wherein the volume of the capillary space is less than about 1 µL.

Process CC

The method of process U wherein the electrochemical test sensor further includes a spacer, the spacer being located between the lid and the reagent layer.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. A test sensor for cooperating with a meter to determine a concentration of an analyte in a fluid test sample, the meter including a light source, the test sensor comprising:

a base;

a reagent adapted to chemically react with the analyte; and a lid attached to the base and forming therebetween a capillary space with an opening for receiving the fluid test sample, the lid including a polymeric light guide and an opaque area at least partially surrounding the polymeric light guide, the polymeric light guide being configured to transmit therethrough light generated by the light source of the meter from a first end of the lid to the capillary space.

2. The test sensor of claim 1, wherein the polymeric light guide extends continuously from the first end of the lid to an opposing second end of the lid.

3. The test sensor of claim 1, wherein the lid has at least one air vent adjacent the polymeric light guide.

4. The test sensor of claim 1, wherein the polymeric light guide is formed from at least one of acrylic, polyethylene terephthalate (PET), or polycarbonate.

5. The test sensor of claim 1, further comprising an electrically conductive counter electrode and an electrically conductive working electrode.

6. The test sensor of claim 5, further comprising an electrically conductive trigger electrode adjacent the counter and working electrodes.

7. The test sensor of claim 5, further comprising a first electrical conductor disposed between the working electrode and the base, and a second electrical conductor disposed between the counter electrode and the base.

8. The test sensor of claim 1, further comprising a dielectric layer between the lid and the base.

9. The test sensor of claim 8, wherein the dielectric layer defines therethrough a dielectric window.

10. The test sensor of claim 1, wherein the volume of the capillary space is less than about 1 µL.

11. The test sensor of claim 1, further comprising a spacer disposed between the lid and the base.

12. The test sensor of claim 1, wherein the reagent includes glucose oxidase or glucose dehydrogenase, or a combination thereof.

13. An analyte testing system for determining a concentration of an analyte in a fluid test sample, the analyte testing system comprising:
    a meter having a light source; and
    a test sensor with a base, a reagent, and a lid, the reagent including an enzyme adapted to chemically react with the analyte, and the lid mating with the base to form therebetween a capillary space with an opening for receiving the fluid test sample,
    wherein the lid includes a polymeric light guide and an opaque area at least partially surrounding the polymeric light guide, the polymeric light guide being configured to transmit light generated by the light source from a first end of the lid to the capillary space.

14. An electrochemical test sensor for electrically connecting with a meter to determine a concentration of an analyte in a fluid test sample, the meter including an electrical current detector and a light source, the electrochemical test sensor comprising:
    a base supporting a counter electrode and a working electrode each configured to electrically communicate with the electrical current detector of the meter;
    a reagent supported by the base adjacent the working and counter electrodes, the reagent including an enzyme adapted to chemically react with the analyte in the fluid test sample; and
    a lid mating with the base to form a capillary space with an opening for receiving the fluid test sample, the lid including a transparent or translucent polymeric light guide at least partially surrounded by an opaque area, the polymeric light guide being configured to transmit light generated by the light source from a first end of the lid to the capillary space at a second end of the lid.

15. The electrochemical test sensor of claim 14, wherein the lid defines therethrough at least one air vent adjacent the polymeric light guide.

16. The electrochemical test sensor of claim 14, wherein the polymeric light guide is embedded in the lid extending continuously between the first and second ends of the lid.

17. The electrochemical test sensor of claim 14, wherein the polymeric light guide is formed from at least one of acrylic, polyethylene terephthalate (PET), or polycarbonate.

18. The electrochemical test sensor of claim 14, further comprising an electrically conductive trigger electrode supported by the base adjacent the counter and working electrodes.

19. The electrochemical test sensor of claim 14, further comprising first and second electrical conductors supported by the base, the first electrical conductor being disposed between the working electrode and the base, and the second electrical conductor being disposed between the counter electrode and the base.

20. The electrochemical test sensor of claim 14, further comprising a dielectric layer between the lid and the base, the dielectric layer defining therethrough a dielectric window.

* * * * *